(12) United States Patent
Sampognaro et al.

(10) Patent No.: US 10,086,176 B2
(45) Date of Patent: Oct. 2, 2018

(54) BALLOON CATHETER AND METHODS FOR USE

(75) Inventors: Gregory Sampognaro, Monroe, LA (US); Gwendolyn Watanabe, Sunnyvale, CA (US); Jeffrey Krolik, Campbell, CA (US)

(73) Assignee: HOTSPUR TECHNOLOGIES, INC., Mountain View, CA (US)

( * ) Notice: Subject to any disclaimer, the term of this patent is extended or adjusted under 35 U.S.C. 154(b) by 0 days.

(21) Appl. No.: 12/966,925

(22) Filed: Dec. 13, 2010

(65) Prior Publication Data

US 2011/0172598 A1 Jul. 14, 2011

Related U.S. Application Data

(60) Provisional application No. 61/284,071, filed on Dec. 11, 2009.

(51) Int. Cl.
| | | |
|---|---|---|
| *A61M 29/00* | (2006.01) |
| *A61M 25/10* | (2013.01) |
| *A61B 17/22* | (2006.01) |
| *A61B 17/3207* | (2006.01) |
| *A61M 25/06* | (2006.01) |
| *A61M 25/00* | (2006.01) |

(52) U.S. Cl.
CPC ......... *A61M 25/1002* (2013.01); *A61B 17/22* (2013.01); *A61B 17/3207* (2013.01); *A61M 25/0068* (2013.01); *A61M 25/0662* (2013.01); *A61B 2017/22001* (2013.01); *A61B 2017/22038* (2013.01); *A61B 2017/22069* (2013.01); *A61B 2017/22094* (2013.01); *A61M 25/008* (2013.01); *A61M 25/0041* (2013.01); *A61M 2025/0681* (2013.01); *A61M 2025/1047* (2013.01); *A61M 2025/1093* (2013.01)

(58) Field of Classification Search
CPC ........ A61B 17/3207; A61B 17/320725; A61B 17/320758; A61B 17/320708; A61B 17/32075; A61B 2017/320716; A61B 2017/320733; A61B 2017/320741; A61B 2017/320766; A61B 2017/320775
USPC .................................................. 606/159, 192
See application file for complete search history.

(56) References Cited

U.S. PATENT DOCUMENTS

| | | | | |
|---|---|---|---|---|
| 4,896,669 A | * | 1/1990 | Bhate ................. | A61M 25/1006 604/103.1 |
| 5,044,369 A | * | 9/1991 | Sahota .............. | A61M 25/0068 600/435 |

(Continued)

*Primary Examiner* — Diane Yabut
*Assistant Examiner* — Martin T Ton
(74) *Attorney, Agent, or Firm* — Baker Hostetler LLP

(57) ABSTRACT

Apparatus and methods are provided for treating a lesion within a body lumen using a catheter including a balloon on its distal end and an abrasive distal tip extending distally beyond the balloon. The distal tip may terminate in a sharpened tip for penetrating occlusive material, e.g., a beveled tip, and includes abrasive material on an outer surface thereof, e.g., abrasive grit, cutting elements, and the like, for abrading occlusive material adjacent the distal tip. The abrasive material may be arranged in a predetermined pattern, e.g., an axial, circumferential, or helical pattern, to facilitate abrading occlusive material. The distal tip may have a substantially uniform diameter or tapered shape along its length.

17 Claims, 3 Drawing Sheets

(56) References Cited

U.S. PATENT DOCUMENTS

| | | | | |
|---|---|---|---|---|
| 5,100,424 | A * | 3/1992 | Jang | A61B 8/12 600/439 |
| 5,250,060 | A * | 10/1993 | Carbo | A61B 17/320725 604/164.13 |
| 5,350,395 | A * | 9/1994 | Yock | A61B 18/245 604/103.04 |
| 6,179,887 | B1 * | 1/2001 | Barber, Jr. | A46B 3/005 451/527 |
| 6,258,108 | B1 * | 7/2001 | Lary | 606/159 |
| 6,824,550 | B1 * | 11/2004 | Noriega et al. | 606/159 |
| 6,929,633 | B2 * | 8/2005 | Evans | A61B 17/22 604/101.04 |
| 6,955,174 | B2 * | 10/2005 | Joye | A61B 1/00082 128/898 |
| 7,367,982 | B2 * | 5/2008 | Nash et al. | 606/159 |
| 2004/0138691 | A1 * | 7/2004 | Goodin | A61M 25/104 606/194 |
| 2005/0119615 | A1 * | 6/2005 | Noriega | A61B 17/320758 604/95.04 |
| 2007/0088230 | A1 * | 4/2007 | Terashi et al. | 600/585 |
| 2007/0225680 | A1 * | 9/2007 | Biggins | A61L 29/06 604/526 |
| 2008/0097247 | A1 * | 4/2008 | Eskuri | 600/585 |
| 2008/0147170 | A1 * | 6/2008 | Vrba | A61M 25/00 623/1.22 |
| 2010/0082051 | A1 * | 4/2010 | Thorpe et al. | 606/159 |

* cited by examiner

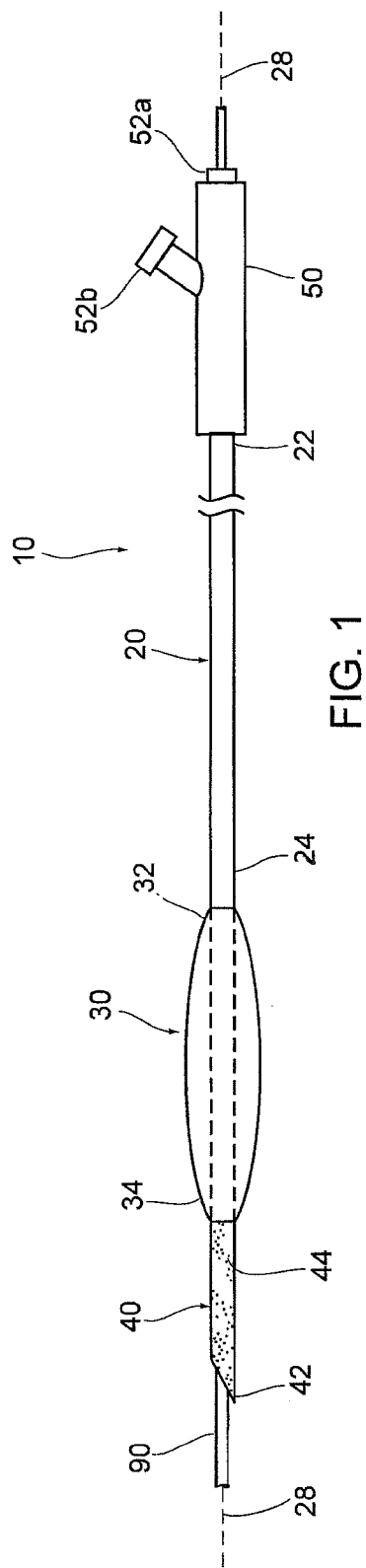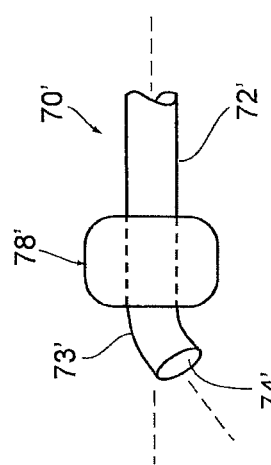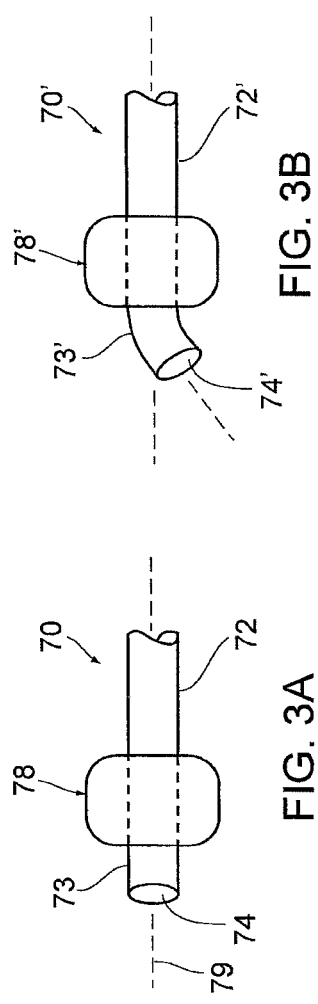

BALLOON CATHETER AND METHODS FOR USE

RELATED APPLICATIONS

This application claims benefit of U.S. provisional application Ser. No. 61/284,071, filed Dec. 11, 2009, the entire disclosure of which is expressly incorporated by reference herein.

FIELD OF THE INVENTION

The present invention relates generally to apparatus and methods for treating stenoses, occlusions, or other lesions within a body lumen of a patient. More particularly, the present invention relates to catheters including a balloon and/or features to enhance treatment of stenoses, occlusions, or other lesions within a body lumen, and to systems and methods for using such catheters.

BACKGROUND

Medical balloons are frequently used in interventional procedures where a vessel with in the body has become constricted. One of the difficulties with conventional balloon catheters is crossing and/or treating high grade stenoses and chronic total occlusions ("CTOs").

Motorized atherectomy devices have been suggested for crossing and/or opening such CTOs. However, such devices may risk damaging the intimal layers of the vessel wall when being directed through calcified plaque or other occlusive material.

Accordingly, apparatus and methods for treating occlusions within blood vessels, grafts, or other body lumens would be useful.

SUMMARY

The present invention is directed to apparatus for treating stenoses, occlusions, or other lesions within a body lumen of a patient. More particularly, the present invention is directed to catheters including a balloon and/or other features to enhance treatment of stenoses, occlusions, or other lesions within a body lumen, and to systems and methods for using such catheters.

In accordance with one embodiment, an apparatus is provided for treating a lesion within a body lumen that includes a tubular member including a proximal end, a distal end sized for introduction into a body lumen, and a lumen extending between the proximal and distal ends; an expandable member on the distal end; and an abrasive distal tip extending distally beyond the expandable member. The distal tip may terminate in a sharpened tip for penetrating occlusive material, e.g., a beveled tip, and/or may include abrasive material on an outer surface thereof, e.g., for abrading occlusive material adjacent the distal tip. For example, the abrasive material may include an abrasive grit, cutting elements, and the like attached or otherwise disposed on the distal tip. The abrasive material may be arranged in a substantially uniform or random manner, or may be arranged in a predetermined pattern, e.g., an axial, circumferential, or helical pattern, to facilitate abrading occlusive material.

The distal tip may have a substantially uniform diameter or other cross-section along its length or may be tapered, e.g., such that the sharpened tip provides a relatively small tip to facilitate penetration into occlusive material.

In accordance with another embodiment, a system is provided for treating a lesion within a body lumen that includes a guide catheter, and a treatment catheter. Generally, the guide catheter includes a proximal end, a distal end sized for introduction into a body lumen, a lumen extending between the proximal and distal ends. Optionally, the guide catheter may include an balloon or other expandable member on the distal end, e.g., for centering or stabilizing the distal end when the expandable member is expanded within a body lumen.

The treatment catheter may include a proximal end, a distal end sized for introduction into a body lumen, a lumen extending between the proximal and distal ends, an expandable member on the distal end, and a distal tip extending beyond the expandable member. The distal tip may terminate in a sharpened tip for penetrating into occlusive material and/or may include abrasive material on an outer surface thereof for abrading occlusive material adjacent the distal tip.

In accordance with still another embodiment, a method is provided for treating a lesion comprising high grade stenosis or chronic total occlusion within a body lumen. A distal end of a tubular member may be introduced into the body lumen with an expandable member thereon in a collapsed condition, e.g., over a guidewire previously placed across the lesion and/or through a guide catheter. An abrasive distal tip of the tubular member may be manually advanced into occlusive material defining the lesion to abrade away sufficient occlusive material to advance the distal tip through the lesion. For example, the catheter may be rotated manually and/or advanced and retracted manually to chip or otherwise remove occlusive material, e.g., similar to a rasp or file. Such manual manipulation of an abrasive tip may be useful for removing calcified or fibrotic occlusive material to create a passage through the lesion with minimal risk of damaging the intimal or other layers of the wall of the vessel being treated.

Once sufficient passage is created, the catheter may be manipulated to place the expandable member across and/or within the lesion. The expandable member may then be expanded within the lesion to dilate the lesion. After sufficient treatment, the expandable member may be collapsed, and the catheter (and/or other components introduced into the body lumen) may be removed.

The apparatus and methods herein may facilitate crossing, dilating, or otherwise treating lesions, particularly high grade stenoses and chronic total occlusions.

Other aspects and features of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments.

FIG. 1 is a side view of an exemplary embodiment of a catheter including a balloon and an abrasive distal tip for facilitating crossing a lesion.

FIG. 3A is a side view of an exemplary embodiment of a guide catheter including an expandable member on a distal end thereof.

FIG. 3B is a side view of an alternative embodiment of a guide catheter including an expandable member on a distal end thereof.

DETAILED DESCRIPTION OF THE EXEMPLARY EMBODIMENTS

Figure 2:
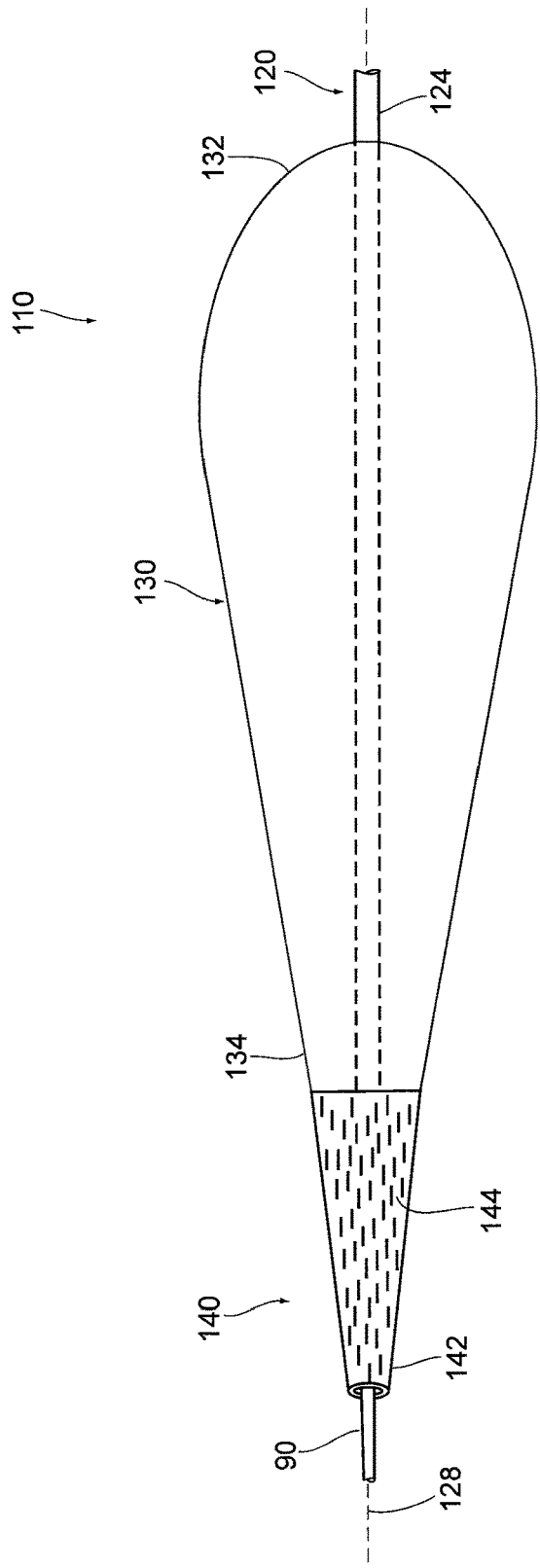
FIG. 2 is a side view of a distal end of another embodiment of a catheter including a balloon and an abrasive distal tip.

Turning to the drawings, FIG. 1 shows an exemplary embodiment of an apparatus 10 for treating a body lumen, e.g., a high grade stenosis, chronic total occlusion, or other lesion within a body lumen, such as a blood vessel, aortovenous fistula, tubular graft, and the like. Generally, the apparatus 10 includes a catheter or other tubular member 20, a balloon or other expandable member 30, and an abrasive tip 40 extending distally beyond the balloon 30. Optionally, the apparatus 10 may include other features, such as a valve (not shown) for infusing and/or aspirating material adjacent the balloon 30, one or more guide catheters 70 (not shown in FIG. 1, see, e.g., FIGS. 3A, 3B), guidewires 90, and/or other devices to provide a system for treating a body lumen.

Generally, the catheter 20 may be an elongate tubular body including a proximal end 22, a distal end 24 sized for introduction into a body lumen, and one or more lumens (not shown) extending between the proximal and distal ends 22, 24, thereby defining a longitudinal axis 28. The catheter 20 may have a substantially uniform construction along its length, or alternatively, the construction may be varied. For example, a proximal portion of the catheter 20 may be substantially rigid or semi-rigid to facilitate advancement of the apparatus 10 by pushing or otherwise manipulating the proximal end. In addition or alternatively, a distal portion of the catheter 20 may be flexible, e.g., to facilitate bending and/or advancement through tortuous anatomy without substantial risk of kinking or buckling. In addition, the catheter 20 may have sufficient torsional rigidity that rotation of the proximal end 22 may transmit to cause rotation of the distal end 24, as described further below. In exemplary embodiments, the catheter 20 may be formed from materials such a metal, plastic, e.g., PEEK, Grilamed L25, and the like, or composite materials. The catheter 20 may have a length between about fifty and one hundred fifty centimeters (50-150 cm) and an outer diameter between about one and two millimeters (1.0-2.0 mm).

As shown, the balloon 30 includes proximal and distal ends 32, 34 attached or otherwise coupled to the distal end 24 of the catheter 20 to provide a fluid-tight connection, e.g., by one or more of bonding with adhesive, interference fit, sonic welding, fusing, engagement with a surrounding sleeve or other connector (not shown), and the like. Alternatively, the balloon 30 may include a proximal end 32 attached to the distal end 24 of the catheter 20, and a distal end spaced distally from the distal end 24, e.g., similar to the apparatus disclosed in application Ser. No. 12/497,135, filed Jul. 2, 2009 and published as U.S. Publication No. 2010/0036410, and Ser. No. 12/843,004, filed Jul. 23, 2010, the entire disclosures of which are expressly incorporated by reference herein. In this alternative, the apparatus 10 may include a valve for selectively opening or closing an outlet, e.g., within or adjacent the distal end 34 or proximal end 32 of the balloon, similar to the apparatus disclosed in these references. In addition or alternatively, the balloon 30 may include one or more features for enhancing treatment of a lesion, e.g., one or more cutting features (not shown), as disclosed in application Ser. No. 12/778,056, filed May 11, 2010 and published as U.S. Publication No. 2010/0286593, the entire disclosure of which is expressly incorporated by reference herein.

The balloon 30 may be expandable from a low profile, collapsed configuration, e.g., folded or otherwise disposed around or against the outer surface of the catheter 20 to facilitate introduction of the catheter 20 into a patient's body, and a high profile, expanded configuration, e.g., to engage or otherwise contact an inner surface of a body lumen within which the catheter is introduced.

The balloon 30 may be formed from substantially inelastic material, e.g., to provide a non-compliant balloon that expands to a predetermined size when inflated independent of pressure (once a minimum volume and/or pressure is introduced to achieve the predetermined size). Such a non-compliant balloon 30 may expand to the predetermined size even if inflated to relatively high pressures, e.g., until the balloon 30 bursts or otherwise ruptures, e.g., at pressures of ten atmospheres, twenty atmospheres, thirty atmospheres, and the like. Alternatively, the balloon 30 may be formed from elastic material, e.g., to provide a compliant or semi-compliant balloon that may be expanded to a variety of sizes and/or shapes, e.g., based on the amount of fluid and/or pressure within the interior 36 of the balloon 30.

Optionally, the catheter 20 may include a handle or hub 50 on the proximal end 22. The handle 50 may be shaped to facilitate holding or manipulating the apparatus 10 and/or may include one or more actuators and/or ports 52. For example, if a valve is provided adjacent the balloon 30, an actuator (not shown) may be provided on the handle 50 for selectively opening and/or closing the valve, e.g., as disclosed in the applications incorporated by reference elsewhere herein.

As shown in FIG. 1, the handle 50 includes a first port 52a that communicates with a first lumen (not shown) that extends through the catheter 20 and the distal tip 40 for receiving a guidewire, elongate rail, or other instrument (not shown). The handle 50 may include one or more seals, e.g., a hemostatic seal, to provide a substantially fluid-tight seal around a guidewire or other instrument received through the port 52a. In addition, a second side port 52b may be provided on the handle 50 that communicates with an inflation lumen (not shown) that extends through the catheter 20 and communicates with an interior of the balloon 30. A source of inflation media and/or vacuum, e.g., a syringe with saline or other fluid (not shown), may be coupled to the side port 52b for delivering inflation media into and/or aspirating inflation media out of the interior for expanding and collapsing the balloon 30. Alternatively, the balloon 30 may be replaced with an expandable member that may be mechanically or otherwise expandable, e.g., including an expandable frame or other structure within or otherwise coupled to a membrane (not shown), or may be eliminated, if desired.

With continued reference to FIG. 1, the distal tip 40 may extend distally from the distal end 24 of the catheter 20 and/or the distal end 34 of the balloon 30 and may terminate in a beveled or other sharpened or pointed tip 42, e.g., to facilitate penetration into and/or through a stenosis or occlusion, as described further below. In addition, the distal tip 40 may include abrasive features 44 on an outer surface thereof, e.g., abrasive material embedded or otherwise attached to a base material of the distal tip 40. For example, the distal tip 40 may include a base tubular body extending from the distal end 34 of the balloon 30 to the beveled tip 42 that has sufficient column strength or other rigidity to allow the distal tip 40 to be directed into occlusive material without substantial risk of buckling or kinking. For example, the distal tip 40 may be formed from a metal, plastic, or composite tube with the beveled tip 42 cut or otherwise formed thereon. The tube may be attached to the distal 24 of the catheter 20 and/or the distal end 34 of the balloon 30, e.g., by one or more of an interference fit, bonding with adhesive, mating connectors, fusing, sonic welding, and the like.

The abrasive material may be embedded directly into the tube or may be attached thereto, e.g., using a binder or other adhesive. The abrasive material may be formed from one or more of metal, diamond or other stone or crystal, glass, aluminum oxide, acrylic or other plastic, and the like. For example, the material may be ground or otherwise provided in powder, grains, or other particles of a desired size and/or shape to provide a desired grit. The abrasive material may be attached to the distal tip 40 in a substantially uniform pattern, a random pattern, or in a pattern to provide desired abrasive characteristics. For example, the abrasive material may be aligned in spaced apart rows extending axially substantially parallel to the longitudinal axis 28, circumferentially or helically around the distal tip 40, and the like, as desired. In addition or alternatively, the features may include a plurality of small blades or other cutting elements attached to the distal tip 40 in a desired pattern.

The distal tip 40 may have a diameter similar to the distal end 24 of the catheter 20, e.g., between about 0.5-2.5 millimeters, or may be smaller than the distal end 24 to facilitate penetration into a lesion, e.g., over a guidewire 90, as described further below. The distal tip 40 may have a substantially uniform diameter or other cross-section along its length, or alternatively, the distal tip 40 may have a tapered shape.

For example, turning to FIG. 2, another embodiment of an apparatus 110 is shown that includes a catheter 120 including a tapered balloon 130 and tapered distal tip 140. Generally, the catheter 120 may be an elongate tubular body including a proximal end (not shown), a distal end 124 sized for introduction into a body lumen, and one or more lumens (not shown) extending therebetween, similar to the previous embodiments. Unlike the previous embodiments, the balloon 130 may have a tapered shape between its proximal and distal ends 132, 134. For example, when fully expanded, the balloon 130 may have a predetermined shape that tapers from a region adjacent the proximal end 132 distally towards the distal end 134. Alternatively, the balloon 130 may be compliant or semi-compliant and/or may include cutting features (not shown), similar to the previous embodiments. Optionally, the apparatus 110 may include a valve (not shown) adjacent the proximal end 132 or the distal end 134 of the balloon 130, or a valve (also not shown) may be provided within or otherwise adjacent the distal tip 140, similar to the previous embodiments.

Unlike the previous embodiment, the distal tip 140 has a nosecone shape that tapers distally from the distal end 134 of the balloon 130 to a tip 142 of the nosecone 140. Thus, the nosecone 140 may provide a tapered transition from the balloon 130, e.g., to provide a relatively small tip 142 for initially penetrating into occlusive material. The tip 142 may be sharpened similar to the previous embodiments, e.g., to facilitate penetration into and/or through occlusive material, as described further below. In addition, the nosecone 140 may include abrasive material 144, e.g., abrasive grit, cutting elements, and the like attached to and/or arranged on the outer surface of the nosecone 140 in a desired pattern, also similar to the previous embodiments.

Turning to FIGS. 3A and 3B, exemplary embodiments of additional devices are shown that may be included in a system including the apparatus 10 or 110. For example, FIG. 3A shows an exemplary embodiment of a guide catheter 70 that may be used for introducing a guidewire 90 and/or the apparatus 10, 110 into a body lumen. Generally, the guide catheter 70 includes a proximal end (not shown), a distal end 72, and one or more lumens 74 extending therebetween. For example, the guide catheter 70 may include a main lumen 74 sized for receiving a guidewire 90 and/or the apparatus 10, 110 therethrough, e.g., having a diameter between about one and three millimeters (1-3 mm).

In addition, the guide catheter 70 may include a balloon 78 on the distal end 72 and an inflation lumen (not shown) extending between the proximal end and distal end 72 of the guide catheter 70 for expanding and/or collapsing the balloon 78. In an exemplary embodiment, the balloon 78 may be an annular balloon attached to or formed around the distal end 72 of the guide catheter 70. The balloon 78 may be formed from compliant or semi-compliant material, which may facilitate centering or otherwise positioning the distal end 72 within a body lumen without damaging the surrounding wall of the body lumen, as described further below. Thus, in this embodiment, a distal tip 73 of the guide catheter 70 beyond the balloon 78 may be arranged to extend substantially axially along a longitudinal axis 79 of the guide catheter 70.

Alternatively, as shown in FIG. 3B, a guide catheter 70' may be provided that includes a distal tip 73' beyond a balloon 78' that includes a tapered and/or curved shape. As shown, the distal tip 73' may include a predetermined curve or bend, e.g., between about twenty five and thirty degrees (25-30°). The distal tip 73' may have a diameter or other cross-section similar to the rest of the distal end 72 or may taper to a smaller diameter (not shown), if desired.

Turning to FIGS. 4A-4E, the apparatus and/or systems herein may be used to treat a lesion 94 within a body lumen 92, e.g., a high grade stenosis or chronic total occlusion within a blood vessel, aorto-venous fistula, tubular graft, and the like. Generally, the apparatus 10 (which may be any of the embodiments described herein) may be introduced into a patient's body, e.g., percutaneously into a vessel within the patient's vasculature, such as the femoral or carotid artery, with the balloon 30 in the collapsed configuration.

Figure 4A:
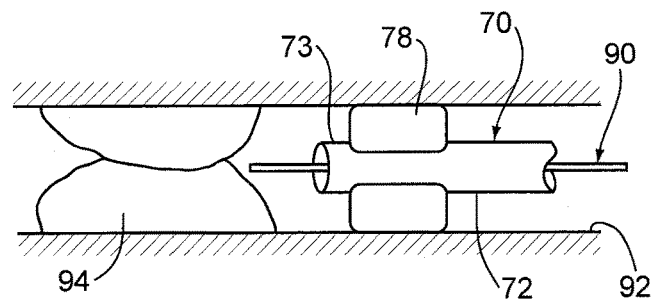
FIGS. 4A-4E are cross-sectional views of a vessel within a patient body including a lesion therein, showing a method for treating the lesion.

For example, as shown in FIG. 4A, a guide catheter 70 may be introduced from a percutaneous entry site through the patient's vasculature until the distal tip 73 is disposed with the target body lumen 92 adjacent the lesion 94, e.g., using conventional procedures. As shown in FIG. 4A, the guide catheter 70 may include a balloon or other expandable member 78 on the distal end 72, although, alternatively, the balloon 78 may be eliminated from the guide catheter 70, if desired.

During introduction, the balloon 78 on the guide catheter 70 may be collapsed against the outer surface of the guide catheter 70 (not shown), e.g., such that the guide catheter 70 may be manipulated similarly to guide catheters without such a balloon. Once the distal tip 73 is positioned at a desired location relative to the lesion 94, the balloon 78 may be expanded, as shown, e.g., to center and/or stabilize the distal tip 73 of the guide catheter 70 within the body lumen 92. A guidewire 90 may then be introduced through the lumen 74 of the guide catheter 70 into the body lumen 90. Using conventional methods, the guidewire 90 may be directed through the lesion 94 until the guidewire 90 crosses entirely through the lesion 94, as shown in FIG. 4B.

Figure 4B:
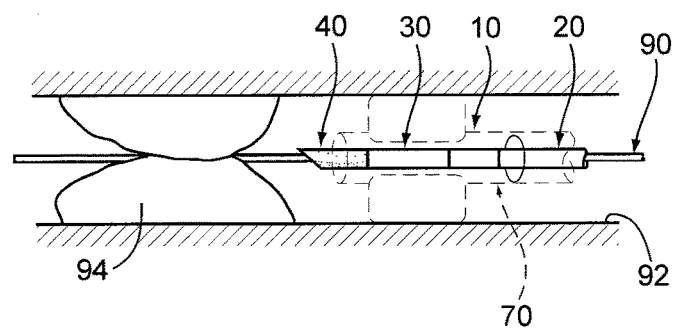

The distal end 24 of the catheter 20 may be advanced through the vasculature, e.g., over the guidewire 90 and/or through the lumen 74 of the guide catheter 70 (shown in phantom for clarity) until disposed within or adjacent the lesion 94, as shown in FIG. 4B. During introduction of the catheter 20, the balloon 30 may remain in a collapsed condition to facilitate advancement through the guide catheter 70 and/or the patient's vasculature. Optionally, if the catheter 20 includes a valve (not shown) at any time during introduction and/or other manipulation of the catheter 20, the valve may be opened to introduce media into the body lumen 92. For example, contrast may be introduced into the lumen 92 to facilitate fluoroscopy or other external imaging to monitor positioning and/or treatment of the lesion 94.

Figure 4C:
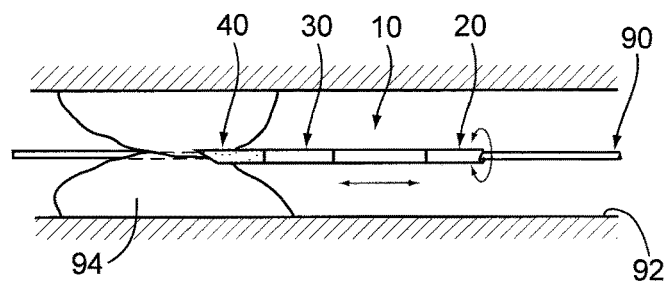

As shown in FIG. 4C (in which the guide catheter has been omitted merely for clarity), once the distal end 24 of the catheter 20 is positioned within the body lumen 92, the abrasive distal tip 40 may be manually advanced into occlusive material defining the lesion 94, e.g., to abrade away sufficient occlusive material to advance the distal tip 40 through the lesion 94. For example, the proximal end (not shown) of the catheter 20 may be rotated manually and/or manually advanced and retracted axially to chip or otherwise remove occlusive material, e.g., similar to a rasp or file. Such rotation and/or axial movement may be transmitted from the proximal end to the distal end 24 and, consequently, to the distal tip 40. For example, the catheter 20 may have sufficient torsional rigidity that rotation may be transmitted to the distal tip 40, e.g., on a one-to-one basis from the proximal end.

Optionally, if the apparatus 10 includes a valve (not shown) adjacent the balloon 30 and/or distal tip 40, the valve may be selectively opened during or between manipulation of the apparatus 10. For example, it may be desirable when crossing the lesion 94 to open the valve to measure pressure adjacent the distal tip 40. Such pressure readings may be obtained as often as desired, e.g., to determine whether the lesion 94 is contributing to low flow through the body lumen 92. For example, if a big pressure drop is detected across the lesion 94, the user may confirm that the lesion 94 is contributing substantially to slowing flow through the body lumen 92, while a low pressure drop may indicate that the lesion 94 is not substantially slowing flow.

It will be appreciated that manual manipulation of the abrasive distal tip 40 may be useful for removing small particles or pieces of calcified or fibrotic occlusive material to create a passage through the lesion 94 with minimal risk of damaging the wall of the body lumen 92, e.g., compared to motorized atherectomy or other devices. Manual manipulation, e.g., in combination with periodic imaging (e.g., enhanced by delivering contrast, if desired), may provide tactile feedback, which may facilitate advancement of the distal tip 40 through the lesion 94. Optionally, fluid may also be delivered via the catheter 20 and/or aspirated to remove any debris released by the abrasive distal tip 40, if desired, e.g., while or after the passage is created.

Figure 4D:
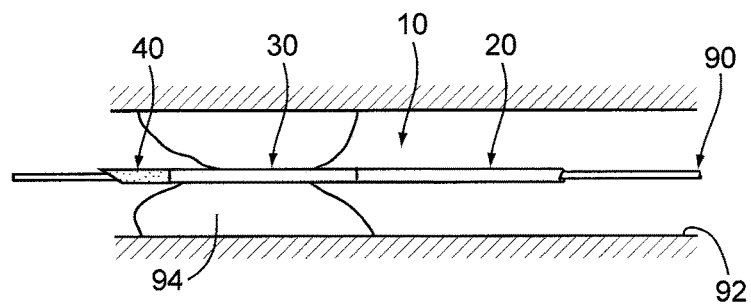
Figure 4E:
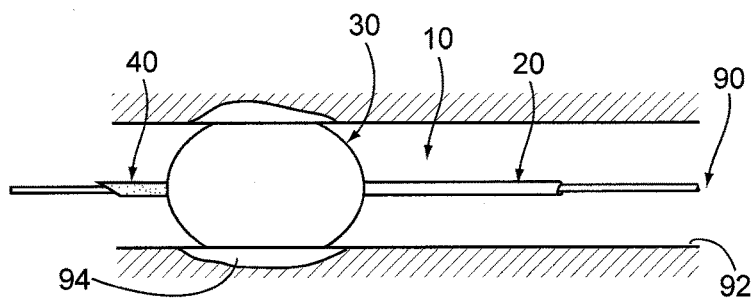

Once sufficient passage is created, as shown in FIG. 4D, the catheter 20 may be manipulated to place the balloon 30, still in the collapsed condition, across and/or within the lesion 94. The balloon 30 may then be expanded within the lesion 94 to dilate the occlusive material and/or surrounding tissue, as shown in FIG. 4E. For example, a syringe or other source of inflation media (not shown) may be used to introduce fluid through the inflation lumen of the catheter 20 to inflate and expand the balloon 30, thereby dilating the lesion 94. If desired, the balloon 30 may be deflated and the process repeated one or more times after moving the catheter 20, e.g., within the same or another body lumen. Thereafter, the balloon 30 may be collapsed and the apparatus 10 withdrawn from the patient's body, e.g., along with any guidewire 90 and/or guide catheter 70, using conventional methods.

In addition, if the apparatus 10 includes a valve, pressure measurements may be obtained before and/or after treating the lesion 94. For example, an initial pressure measurement may be obtained with the apparatus 10 when the distal end 24 of the catheter 20 is initially introduced into the body lumen 92, e.g., to identify pressure characteristics of the lesion 94. After treating the lesion 94, additional pressure measurement(s) may be obtained, which may be compared with the initial pressure measurement, e.g., to confirm that the lesion 94 has been treated sufficiently. For example, a differential in wave form of the pressure may be lower after successful treatment than before. In addition or alternatively, pressure characteristics of the body lumen 92 after treating the lesion 94 may facilitate identifying the body lumen 92, e.g., if the apparatus 10 is subsequently reintroduced into the body lumen 92. It will be appreciated that pressure measurements may be obtained at any other desired time during introduction and/or manipulation of the apparatus 10 before its removal from the patient's body for any other desired purpose if a valve and pressure lumen are provided in the apparatus 10, as described above and in the applications incorporated by reference elsewhere herein.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An apparatus for treating a lesion within a body lumen, the apparatus comprising:
   a tubular member comprising a substantially rigid or semi-rigid proximal end, a flexible distal end sized for introduction into a body lumen, a first lumen for receiving a guidewire extending between the proximal and distal ends of the tubular member, and an inflation lumen for delivering or aspirating inflation media extending between the proximal and distal ends of the tubular member;
   an expandable member on the distal end of the tubular member, the expandable member formed of a substantially inelastic material, the expandable member comprising a proximal end and a distal end, and the expandable member being configured to radially expand entirely between the proximal end and the distal end of the expandable member from a collapsed configuration to an expanded configuration;
   an opening on the distal end of the tubular member within the expandable member in fluid communication with the inflation lumen for delivering or aspirating the inflation media;
   a handle comprising a first port in fluid communication with the first lumen, a hemostatic seal within the first port for providing a substantially fluid-tight seal around the guidewire, and a second port in fluid communication with the inflation lumen; and
   wherein the distal tip of the abrasive distal tip member is beveled an abrasive distal tip member extending distally from the expandable member, the abrasive distal tip member having sufficient column strength or rigidity to be directed into occlusive material without substantial risk of buckling or kinking, the abrasive distal tip member comprising a proximal end, a distal tip, and a lumen extending between the proximal end and the distal tip of the abrasive distal tip member, wherein:

the proximal end of the abrasive distal tip member contacts the distal end of the expandable member, wherein the distal tip of the abrasive distal tip member is beveled the abrasive distal tip member further comprises abrasive material on an outer surface thereof for abrading the occlusive material adjacent the abrasive distal tip member, the abrasive distal tip member has a substantially uniform outer diameter along its length, the substantially uniform outer diameter of the abrasive distal tip member being equal to an outer diameter of the distal end of the tubular member and to an outer diameter of the expandable member when in the collapsed configuration, and the first lumen extending between the proximal and distal ends of the tubular member is in fluid communication with the lumen extending between the proximal end and the distal tip of the abrasive distal tip member.

2. The apparatus of claim 1, wherein the abrasive material comprises abrasive grit or cutting elements attached to the abrasive distal tip member.

3. The apparatus of claim 1, wherein the abrasive material defines an axial pattern, a circumferential pattern, or a helical pattern.

4. The apparatus of claim 1, wherein the tubular member has a predetermined torsional rigidity between the tubular member proximal and distal ends such that rotational movement of the tubular member proximal end is translated to rotational movement of the distal tip.

5. The apparatus of claim 4, wherein the predetermined torsional rigidity causes substantially one-to-one rotational movement between the tubular member proximal end and the distal tip.

6. The apparatus of claim 1, wherein the tubular member is a treatment catheter.

7. The apparatus of claim 1, wherein the beveled distal tip of the abrasive distal tip member terminates in a sharp point.

8. The apparatus of claim 1, wherein the abrasive distal tip member is formed from a metal, plastic, or composite tube.

9. The apparatus of claim 1, wherein the abrasive material has a random pattern on the outer surface of the abrasive distal tip member.

10. A system for treating a lesion within a body lumen, the system comprising:

a guidewire sized for introduction into a body lumen;

a guide catheter comprising a substantially rigid or semi-rigid proximal end, a flexible distal end sized for introduction into the body lumen, and a lumen for receiving the guidewire and a treatment catheter extending between the proximal and distal ends of the guide catheter;

an annular balloon on the distal end of the guide catheter for centering or stabilizing the distal end of the guide catheter when the annular balloon is expanded within the body lumen;

the treatment catheter comprising a proximal end, a distal end sized for introduction through the lumen of the guide catheter into the body lumen, a first lumen for receiving the guidewire extending between the proximal and distal ends of the treatment catheter, and an inflation lumen for delivering or aspirating inflation media extending between the proximal and distal ends of the treatment catheter;

an expandable member on the distal end of the treatment catheter, the expandable member comprising a proximal end and a distal end, and the expandable member formed of a substantially inelastic material, the expandable member being configured to radially expand entirely between the proximal end and the distal end of the expandable member from a collapsed configuration to an expanded configuration;

an opening on the distal end of the treatment catheter within the expandable member in fluid communication with the inflation lumen for delivering or aspirating the inflation media;

a handle comprising a first port in fluid communication with the first lumen, a hemostatic seal within the first port for providing a substantially fluid-tight seal around the guidewire, and a second port in fluid communication with the inflation lumen; and an abrasive distal tip member extending distally from the expandable member, the abrasive distal tip member having sufficient column strength or rigidity to be directed into occlusive material without substantial risk of buckling or kinking, the abrasive distal tip member comprises a proximal end and a distal tip, and a lumen extending between the proximal end and the distal tip of the abrasive distal tip member, wherein:

the proximal end of the abrasive distal tip member contacts the distal end of the expandable member, the abrasive distal tip member has a substantially uniform outer diameter along its length, the substantially uniform outer diameter of the abrasive distal tip member being equal to an outer diameter of the distal end of the treatment catheter and to an outer diameter of the expandable member when in the collapsed configuration, and the first lumen of the treatment catheter is in fluid communication with the lumen of the abrasive distal tip member.

11. The system of claim 10, wherein the abrasive distal tip member comprises abrasive material on an outer surface thereof for abrading occlusive material adjacent the abrasive distal tip member.

12. The system of claim 11, wherein the abrasive material comprises abrasive grit or cutting elements attached to the abrasive distal tip member.

13. The system of claim 11, wherein the abrasive material defines an axial pattern, a circumferential pattern, or a helical pattern.

14. The system of claim 11, wherein the abrasive material has a random pattern on the outer surface of the abrasive distal tip member.

15. The system of claim 10, wherein the guide catheter distal end has a predetermined bend.

16. The system of claim 1, wherein the beveled distal tip of the abrasive distal tip member terminates in a sharp point.

17. The system of claim 10, wherein the abrasive distal tip member is formed from a metal, plastic, or composite tube.

* * * * *